(12) United States Patent
Spangler et al.

(10) Patent No.: US 11,096,716 B2
(45) Date of Patent: Aug. 24, 2021

(54) ATHERECTOMY MEDICAL DEVICE

(71) Applicant: BOSTON SCIENTIFIC SCIMED, INC., Maple Grove, MN (US)

(72) Inventors: David Gordon Spangler, New Richmond, WI (US); Laszlo Trent Farago, Hudson, WI (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 282 days.

(21) Appl. No.: 16/276,354

(22) Filed: Feb. 14, 2019

(65) Prior Publication Data

US 2019/0247084 A1 Aug. 15, 2019

Related U.S. Application Data

(60) Provisional application No. 62/631,372, filed on Feb. 15, 2018.

(51) Int. Cl.
*A61B 17/3207* (2006.01)
*A61B 17/32* (2006.01)

(52) U.S. Cl.
CPC .. *A61B 17/320758* (2013.01); *A61B 17/3207* (2013.01); *A61B 17/320725* (2013.01); *A61B 2017/320004* (2013.01); *A61B 2017/320716* (2013.01); *A61B 2017/320741* (2013.01)

(58) Field of Classification Search
CPC .............. A61B 17/3207; A61B 17/32; A61B 17/320758; A61B 17/320004; A61B 2017/320716; A61B 2017/320741; A61B 17/320725
See application file for complete search history.

(56) References Cited

U.S. PATENT DOCUMENTS

| | | | |
|---|---|---|---|
| 6,126,667 A | 10/2000 | Barry et al. | |
| 6,632,230 B2* | 10/2003 | Barry | A61B 17/320758 604/46 |
| 6,818,001 B2 | 11/2004 | Wulfman et al. | |
| 2005/0015021 A1 | 1/2005 | Shiber | |
| 2015/0335348 A1* | 11/2015 | Cohen | A61B 17/320758 606/159 |
| 2016/0346003 A1 | 12/2016 | Grothe et al. | |
| 2020/0069324 A1* | 3/2020 | Deepa | A61B 17/22012 |

FOREIGN PATENT DOCUMENTS

| | | |
|---|---|---|
| WO | 0051511 A1 | 9/2000 |
| WO | 2014106847 A1 | 7/2014 |

OTHER PUBLICATIONS

International Search Report and Written Opinion dated Apr. 17, 2019 for International Application No. PCT/US2019/018121.

* cited by examiner

*Primary Examiner* — George J Ulsh
(74) *Attorney, Agent, or Firm* — Seager, Tufte & Wickhem, LLP (57) ABSTRACT

Medical devices and methods for using medical devices are disclosed. A rotational atherectomy device may include an elongate drive coil having a proximal end region and a distal end region, the elongate drive coil having a coil winding extending in a first helical direction, the elongate drive coil having a coil pitch. A tubular member is welded to the distal end region of the elongate drive coil via one or more helical welds that extend helically at least part way around the tubular member and a cutting member welded to the tubular member.

17 Claims, 11 Drawing Sheets

ATHERECTOMY MEDICAL DEVICE

CROSS-REFERENCE TO RELATED APPLICATIONS

This application claims the benefit of priority under 35 U.S.C. § 119 of U.S. Provisional Application No. 62/631,372, filed Feb. 15, 2018, the entire disclosure of which is hereby incorporated by reference.

TECHNICAL FIELD

The present disclosure pertains to medical devices, and methods for manufacturing and using medical devices. More particularly, the disclosure is directed to devices and methods for removing occlusive material from a body lumen. Further, the disclosure is directed to an atherectomy device for forming a passageway through an occlusion of a body lumen, such as a blood vessel.

BACKGROUND

Many patients suffer from occluded arteries and other blood vessels which restrict blood flow. Occlusions can be partial occlusions that reduce blood flow through the occluded portion of a blood vessel or total occlusions (e.g., chronic total occlusions) that substantially block blood flow through the occluded blood vessel. In some cases a stent may be placed in the area of a treated occlusion. However, restenosis may occur in the stent, further occluding the vessel and restricting blood flow. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion. A need remains for alternative atherectomy devices to facilitate crossing an occlusion.

SUMMARY

This disclosure provides design, material, manufacturing method, and use alternatives for medical devices. For example, the disclosure is directed to an atherectomy device that includes an elongate shaft having a proximal end region and a distal end region, with a longitudinal axis extending therebetween. A strain relief member is secured to the distal end region of the elongate shaft. A cutting member is secured to the strain relief member and defines an outer surface.

Additionally or alternatively, the elongate shaft may include a drive coil having a plurality of coil windings extending in a first helical direction relative to the longitudinal axis.

Additionally or alternatively, the strain relief member may include a tubular member welded to the drive coil via one or more welds that span multiple coil windings.

Additionally or alternatively, the one or more welds securing the tubular member to the drive coil may extend helically at least partially around the tubular member.

Additionally or alternatively, the one or more welds securing the tubular member to the drive coil may be angled in the first helical direction, but at a different pitch.

Additionally or alternatively, the one or more welds securing the tubular member to the drive coil may be angled in a second helical direction different from the first helical direction.

Additionally or alternatively, the elongate shaft may include a stainless steel.

Additionally or alternatively, the strain relief member may include a stainless steel.

Additionally or alternatively, the strain relief member may include a stainless steel.

Additionally or alternatively, the atherectomy device may further include an abrasive material disposed on at least a portion of the outer surface of the cutting member.

Another example of the disclosure is an atherectomy device that includes an elongate drive coil having a proximal end region and a distal end region, the elongate drive coil having a coil winding extending in a first helical direction, the elongate drive coil having a coil pitch. A tubular member is welded to the distal end region of the elongate drive coil via one or more helical welds that extend helically at least part way around the tubular member. A cutting member is welded to the tubular member.

Additionally or alternatively, the cutting member may include a curved cutting surface and an annular mounting surface, and the cutting member may be welded to the tubular member via one or more welds extending through the annular mounting surface.

Additionally or alternatively, the one or more welds extending through the annular mounting surface may include a circumferential weld extending about the annular mounting surface.

Additionally or alternatively, the one or more welds extending through the annular mounting surface may include a plurality of distinct welds.

Additionally or alternatively, the one or more helical welds may each intersect a plurality of adjacent coil windings.

Additionally or alternatively, the one or more helical welds may each extend in the first helical direction, but at a different pitch than the coil pitch.

Additionally or alternatively, the atherectomy device may further include an abrasive material disposed on at least a portion of the cutting member.

Another example of the disclosure is an atherectomy device that includes an elongate drive coil having a proximal end region and a distal end region, the elongate drive coil having a longitudinal axis and a coil pitch relative to the longitudinal axis. A tubular member is welded to the distal end region of the elongate drive coil via one or more helical welds that extend helically at least part way around the tubular member, the one or more helical welds extending at a weld pitch relative to the longitudinal axis. A cutting member is welded to the tubular member.

Additionally or alternatively, the weld pitch may be different from the coil pitch such that at least one of the one or more helical welds engage a plurality of adjacent coil windings.

Additionally or alternatively, the cutting member may include an abrasive cutting surface.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Many patients suffer from occluded arteries, other blood vessels, and/or occluded ducts or other body lumens which may restrict bodily fluid (e.g. blood, bile, etc.) flow. Occlusions can be partial occlusions that reduce blood flow through the occluded portion of a blood vessel or total occlusions (e.g., chronic total occlusions) that substantially block blood flow through the occluded blood vessel. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion. Ideally, the cutting element excises the occlusion without damaging the surrounding vessel wall and/or a previously implanted stent where restenosis has occurred. However, in some instances the cutting element may be manipulated and/or advanced such that it contacts the vessel wall and/or the stent. Therefore, it may be desirable to utilize materials and/or design an atherectomy device that can excise an occlusion without damaging the surrounding vessel and/or a previously implanted stent where restenosis has occurred. Additionally, it may be desirable that a cutting element be useful in removing hard occlusive material, such as calcified material, as well as softer occlusive material. The methods and systems disclosed herein may be designed to overcome at least some of the limitations of previous atherectomy devices while effectively excising occlusive material. For example, some of the devices and methods disclosed herein may include cutting elements with unique cutting surface geometries and/or designs.

Figure 1:
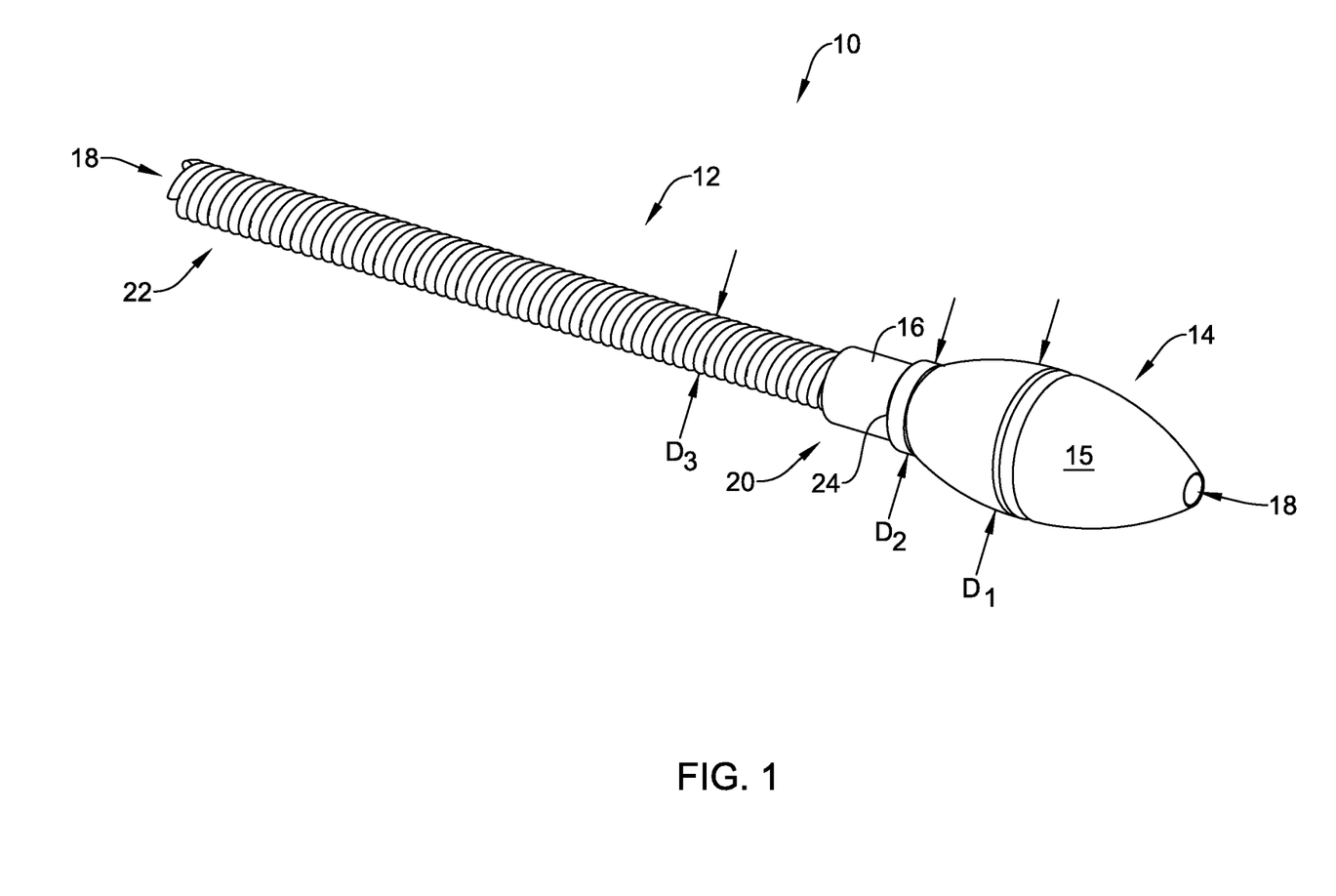
FIG. 1 is a perspective view of an example atherectomy device.
Figure 2:
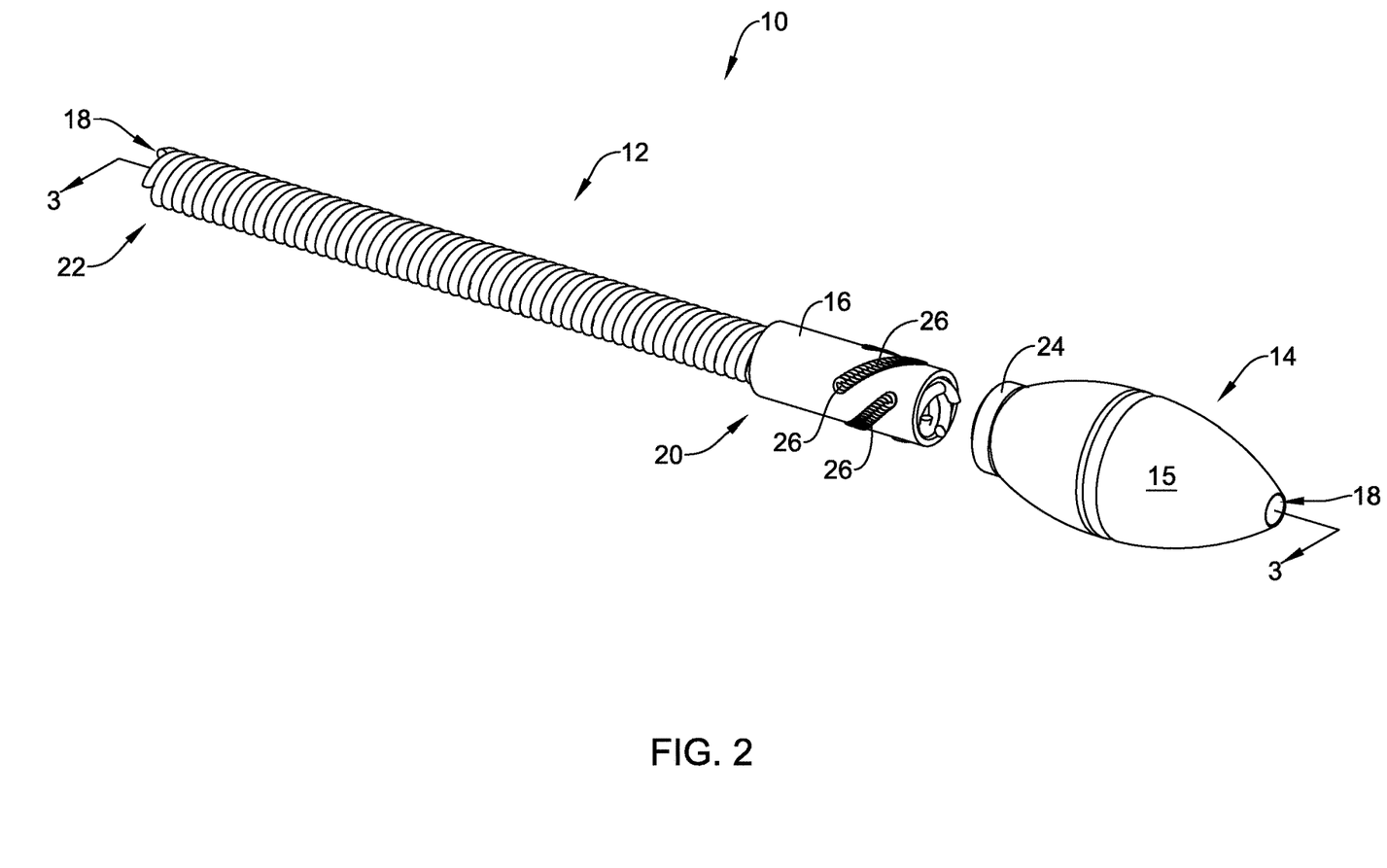
FIG. 2 is a partially exploded perspective view of the example atherectomy device of FIG. 1.
Figure 3:
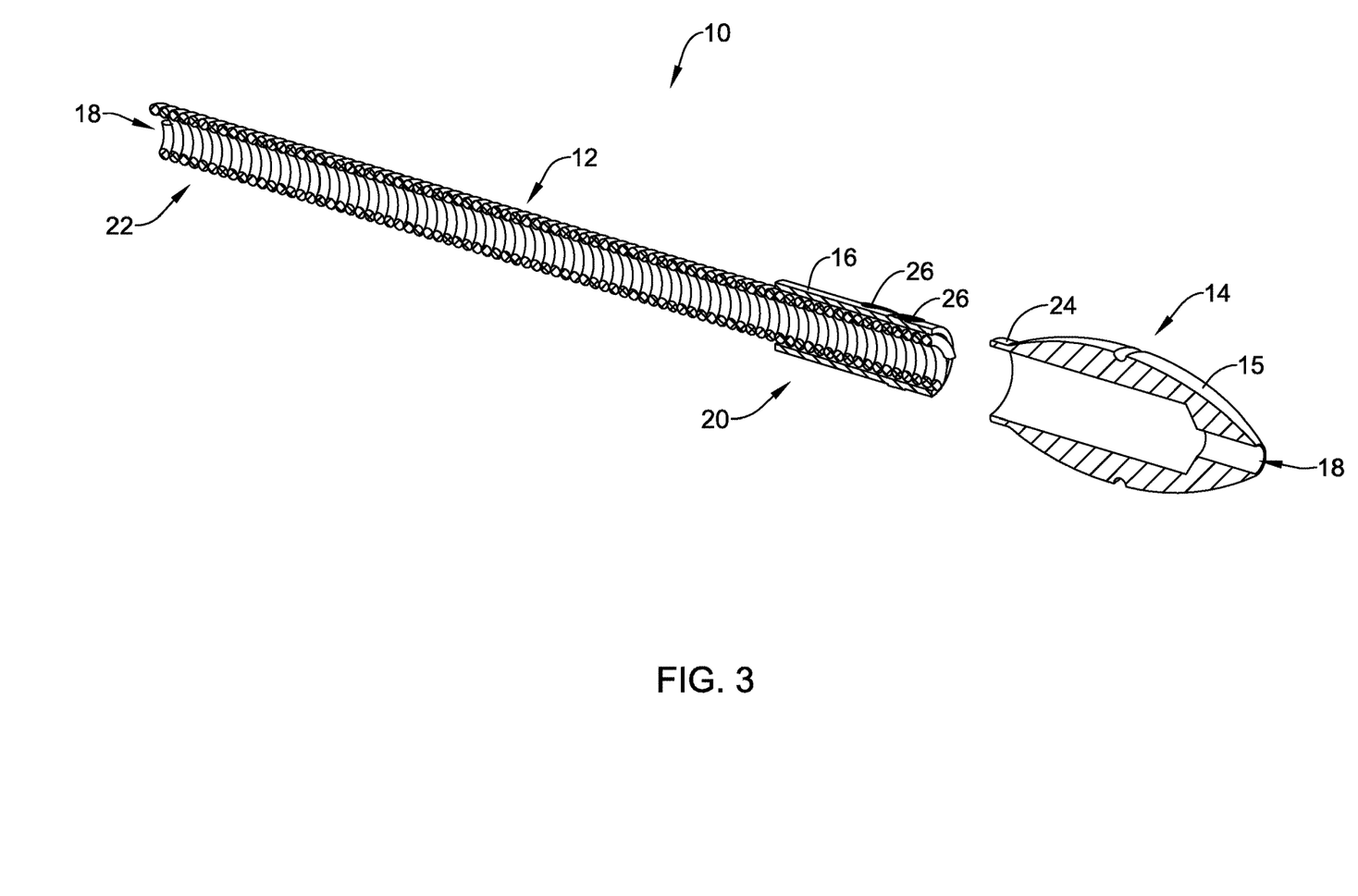
FIG. 3 is a cross-sectional view of the example atherectomy device, taken along line 3-3 of FIG. 2.
Figure 4:
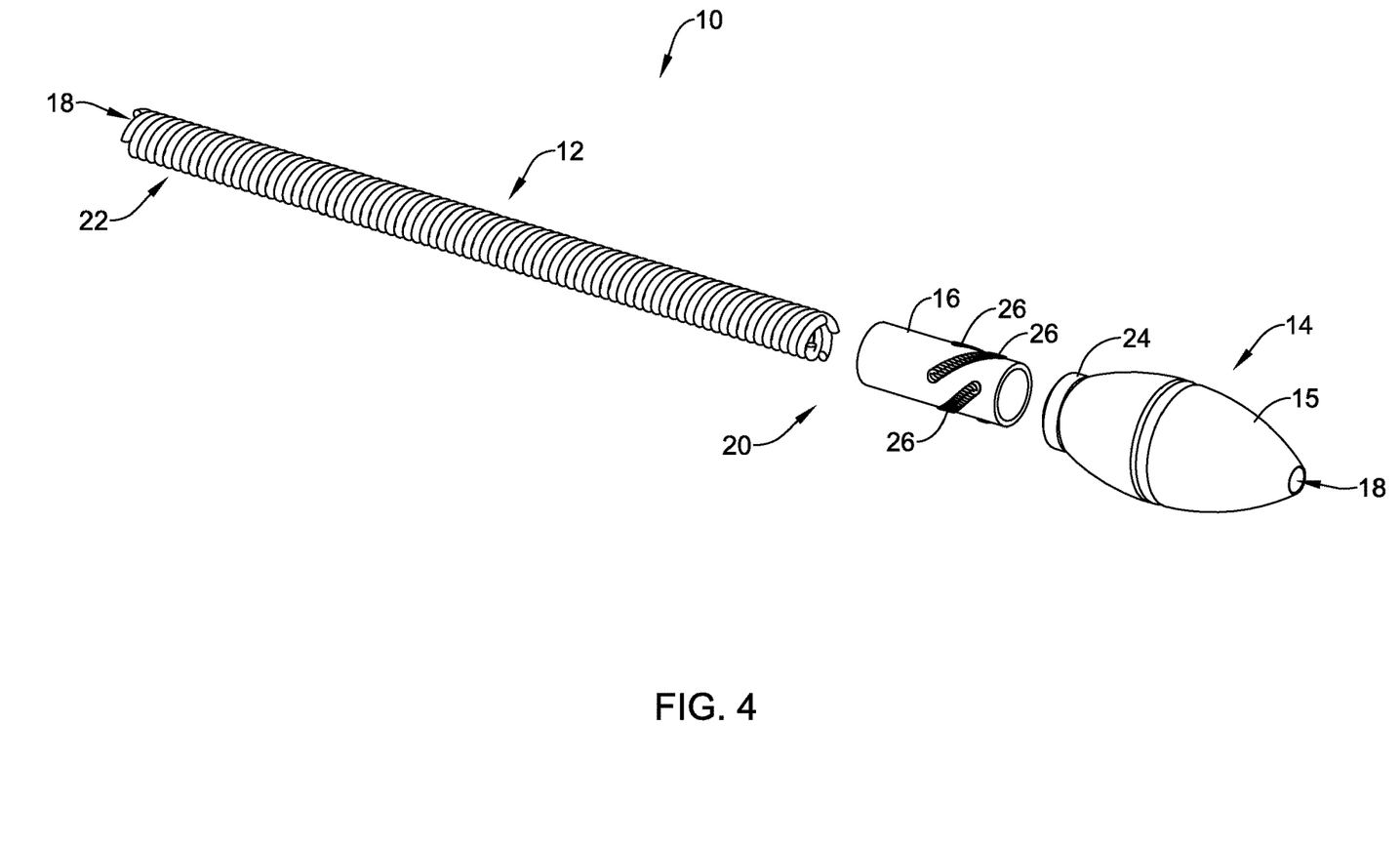
FIG. 4 is a fully exploded perspective view of the example atherectomy device of FIG. 1.

FIG. 1 is a perspective view of an example atherectomy device 10. FIG. 2 is a partially exploded perspective view of the atherectomy device 10, FIG. 3 is a cross-sectional view taken along line 3-3 of FIG. 2 and FIG. 4 is a fully exploded perspective view of the atherectomy device 10. The atherectomy device 10 includes an elongate shaft 12 and a cutting member 14 that is coupled to the elongate shaft 12. In some instances, the cutting member 14 includes an outer surface 15. While shown generically, in some cases the outer surface 15 may include an abrasive material that is adhesively or otherwise secured to the outer surface 15. For example, the outer surface 15 or at least a portion thereof may include diamond coat. In other cases, the outer surface 15 may define any number of different cut patterns formed into the outer surface 15, as desired.

In some cases, the elongate shaft 12 may be a drive coil that is formed from one or more coils wrapped together. In some instances, the drive coil may include only a single coil or filar, or may include a plurality of filars. For example, the drive coil may include 3 to 5 filars. The drive coil may have a single layer, or multiple layers. These are just examples. In some cases, as illustrated, a strain relief member 16 may be disposed between the elongate shaft 12 and the cutting member 14. In some cases, the strain relief member 16 may be considered as being a coupler tube, and in some cases facilitates securement of the cutting member 14 to the elongate shaft 12 by reducing stress concentration and by eliminating bending on a single plane. While described within the context of an atherectomy device, it will be appreciated that use of the strain relief member 16 may be applicable to a variety of different applications in which high speed rotating devices utilize coils as a power transfer media.

In some cases, a lumen 18 extends through the cutting member 14 and the elongate shaft 12. The elongate shaft 12 may be considered as extending from a distal end region 20 to a proximal end region 22. The proximal end region 22 is not shown in its entirety, as it will be appreciated that the particular configuration of the proximal end region 22 of the elongate shaft 12 may vary in accordance with the drive mechanism and other features of an atherectomy system with which the atherectomy device 10 may be used.

Figure 10:
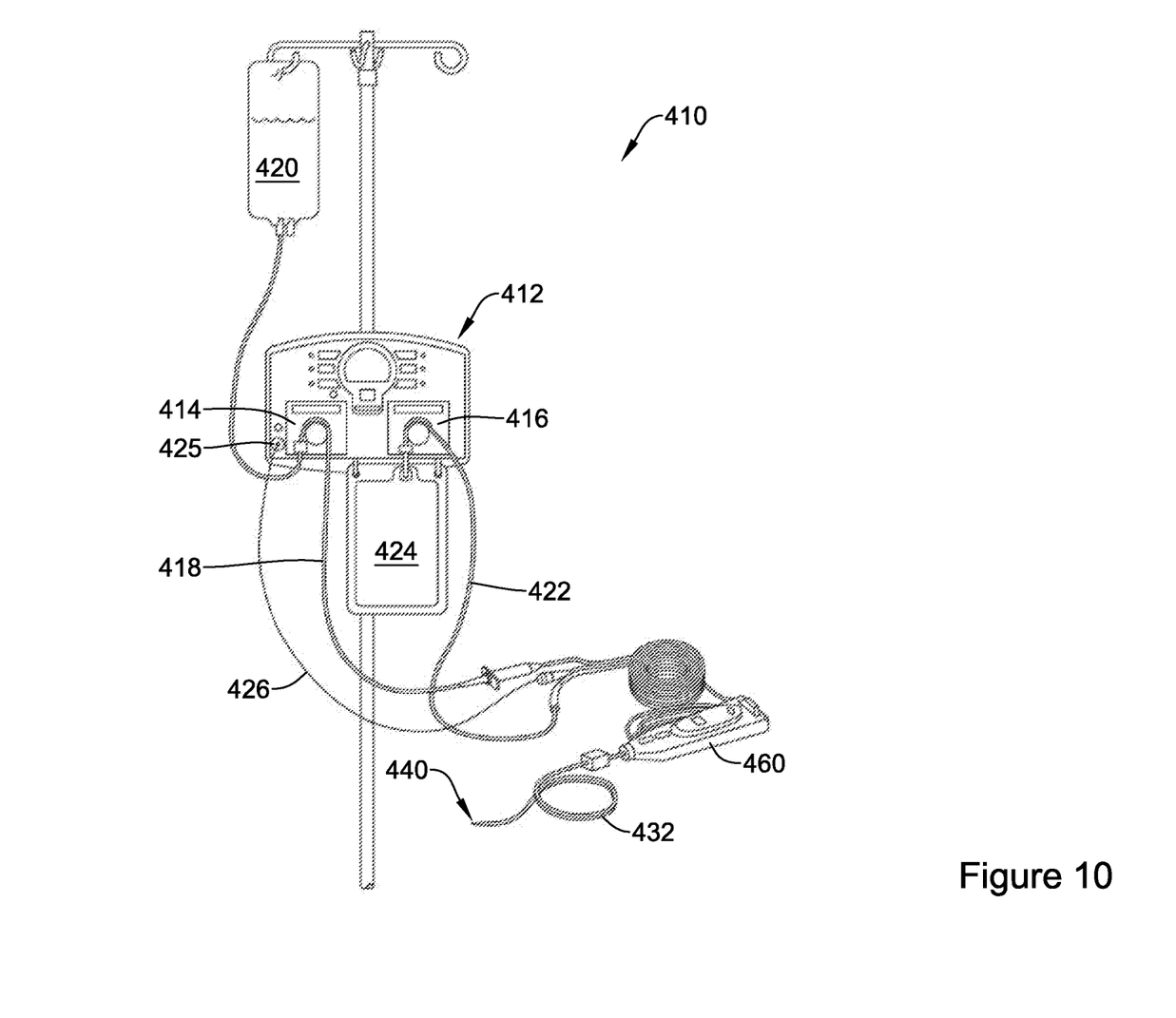
FIG. 10 is a schematic diagram of an example atherectomy system that may utilize any of the atherectomy devices of FIG. 1 through FIG. 9.
Figure 11:
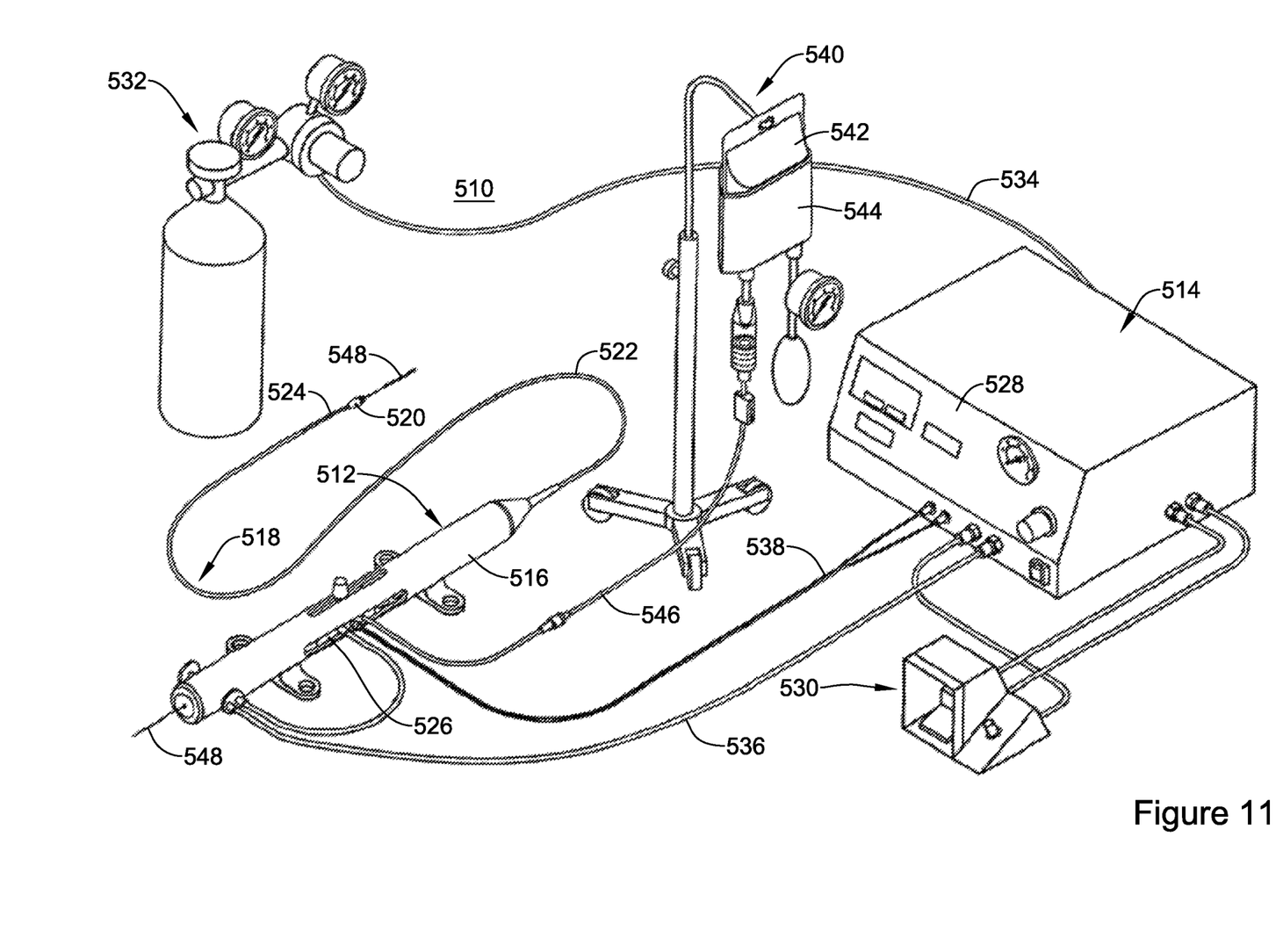
FIG. 11 is a schematic diagram of another exemplary atherectomy system that may utilize any of the atherectomy devices of FIG. 1 through FIG. 9.

As will be discussed, FIG. 10 illustrates an illustrative but non-limiting atherectomy system with which the atherectomy device 10 may be used. FIG. 11 illustrates another illustrative but non-limiting atherectomy system with which the atherectomy device 10 may be used.

Returning to FIG. 1 through FIG. 4, in some cases, the outer surface 15 may be curved, with a maximum diameter that is indicated for example on FIG. 1 as a diameter D1, and that reduces to an annular mounting portion 24 having a diameter that is indicated for example on FIG. 1 as a diameter D2. The diameter D2 is less than the diameter D1, but is itself larger than a diameter of the elongate shaft 12 that is indicated for example on FIG. 1 as a diameter D3. In some cases, providing the elongate shaft 12 with a smaller diameter than that of the cutting member 14 may mean that the cutting member 14 may be dimensioned to fully contact a possible occlusion across a full dimension of the possible occlusion while the elongate shaft 12 may be smaller in diameter than the blood vessel bearing the possible occlusion, thereby reducing potential frictional issues as the elongate shaft 12 rotates. In some instances, the diameter D1 of the cutting member 14 may be up to 5 percent larger than the diameter D3 of the elongate shaft 12. In some cases, D1 may be up to 10 percent larger than D3, or even larger.

As will be discussed, in some cases the strain relief member 16 may be welded to the elongate shaft 12, and the cutting member 14 may be welded to the elongate shaft 12. In some cases, the strain relief member 16, by virtue of being welded to multiple coils on the elongate shaft 12, helps to reduce stress concentration by preventing bending on a single plane. As can be seen in FIG. 2 through FIG. 4, the strain relief member 16 may be welded to the elongate shaft 12 via several helically arranged welds 26. In some cases, the helically arranged welds 26 may be performed via laser welding, although other welding processes are contemplated. For example, the helically arranged welds 26 may be performed via micro-pulse arc welding. As can be seen, each of the helically arranged welds 26 extend at least partially around the periphery of the strain relief member 16. In some cases, each of the helically arranged welds 26 contact multiple coils of the elongate shaft 12, thereby providing additional contact points that help reduce stress concentrations that could otherwise occur.

Figure 5:
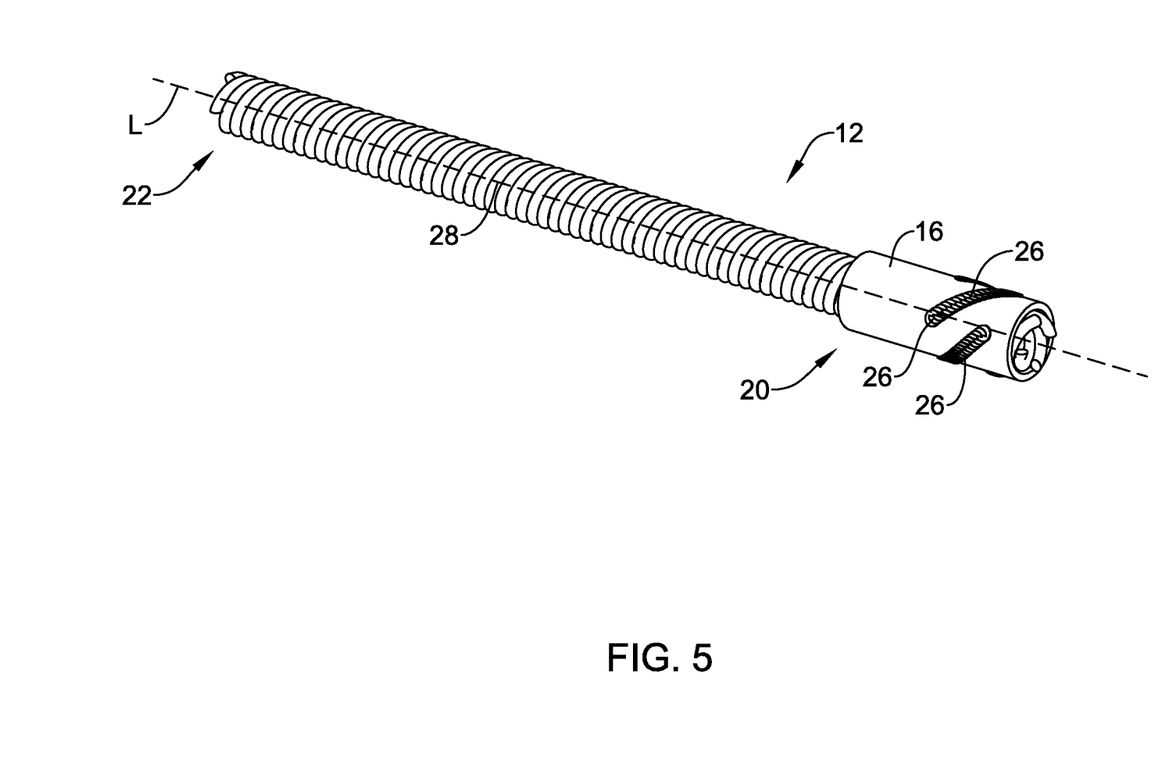
FIG. 5 is a perspective view of a portion of the example atherectomy device of FIG. 1.
Figure 6:
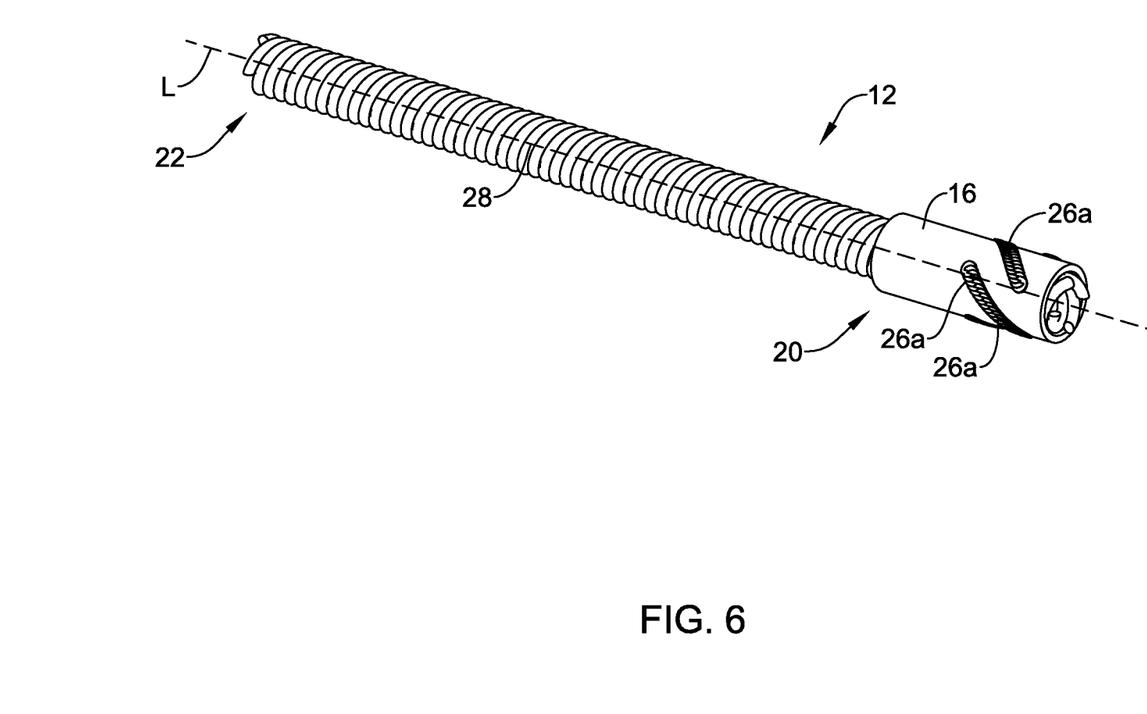
FIG. 6 is a perspective view of a portion of an example atherectomy device similar to that of FIG. 5, but with an another welding pattern.

FIG. 5 and FIG. 6 provide further details regarding how the helically arranged welds 26 may contact multiple coils of the elongate shaft 12. FIG. 5 is a side view of the atherectomy system 10, with the cutting member 14 removed for clarity. Individual coils 28 may be considered as defining a coil pitch, or angle relative to a longitudinal axis L. The helically arranged welds 26 may also be considered as defining a weld pitch, or angle relative to the longitudinal axis L. In some cases, the helically arranged welds 26 may extend all the way around, or substantially all the way around, the strain relief member 16. It will be appreciated that the number of helically arranged welds 26, the weld angle at which the helically arranged welds 26 are disposed and the overall length of each of the helically arranged welds 26 may vary. The weld pitch may be in the same direction of the coil pitch, as illustrated by the helically arranged welds 26 shown in FIG. 5, or may be in an opposite direction of the coil pitch, as illustrated by the helically arranged welds 26 shown in FIG. 6. The weld pitch may vary from a zero degree of offset, relative to the coil pitch, to an offset of plus or minus 90 degrees.

Figure 7:
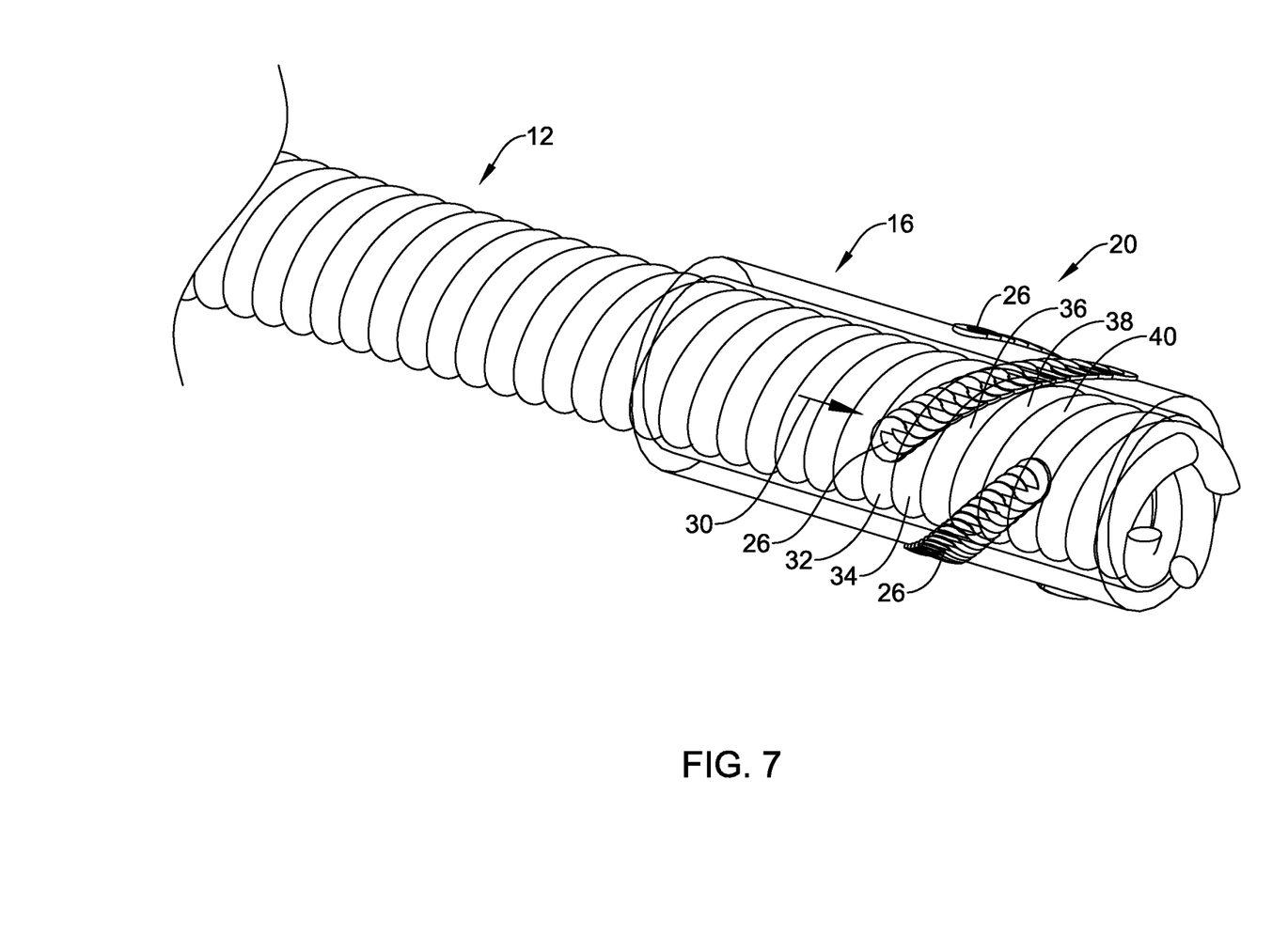
FIG. 7 is an enlarged perspective view of a portion of the example atherectomy device of FIG. 5, with the cutting member shown in phantom to illustrate the welding pattern relative to the coil windings.

In some cases, each of the helically extending welds 26 (or 26a) engage multiple coil windings. This is illustrated in FIG. 7, which shows the strain relief member 16 in phantom and positioned relative to the distal end region 20 of the elongate shaft 12. As an example, a particular helically extending weld 26, denoted by an arrow 30, engages a total of five adjacent coil windings denoted as windings 32, 34, 36, 38 and 40. As will be appreciated, this helps to lessen stress concentrations that could otherwise occur. In some instances, the number of helically extending welds 26 and/or the overall shape of the helically extending welds 26 may vary. In some cases, some of the helically extending welds 26 may extend in a first helical direction (as in FIG. 5) and some of the helically extending welds 26 may extend in a second, different, helical direction (as in FIG. 6). These are just examples. In some cases, the helically extending welds 26 do not fully penetrate the strain relief 16, and thus do not impact the individual filars forming the elongate shaft 12.

Figure 8:
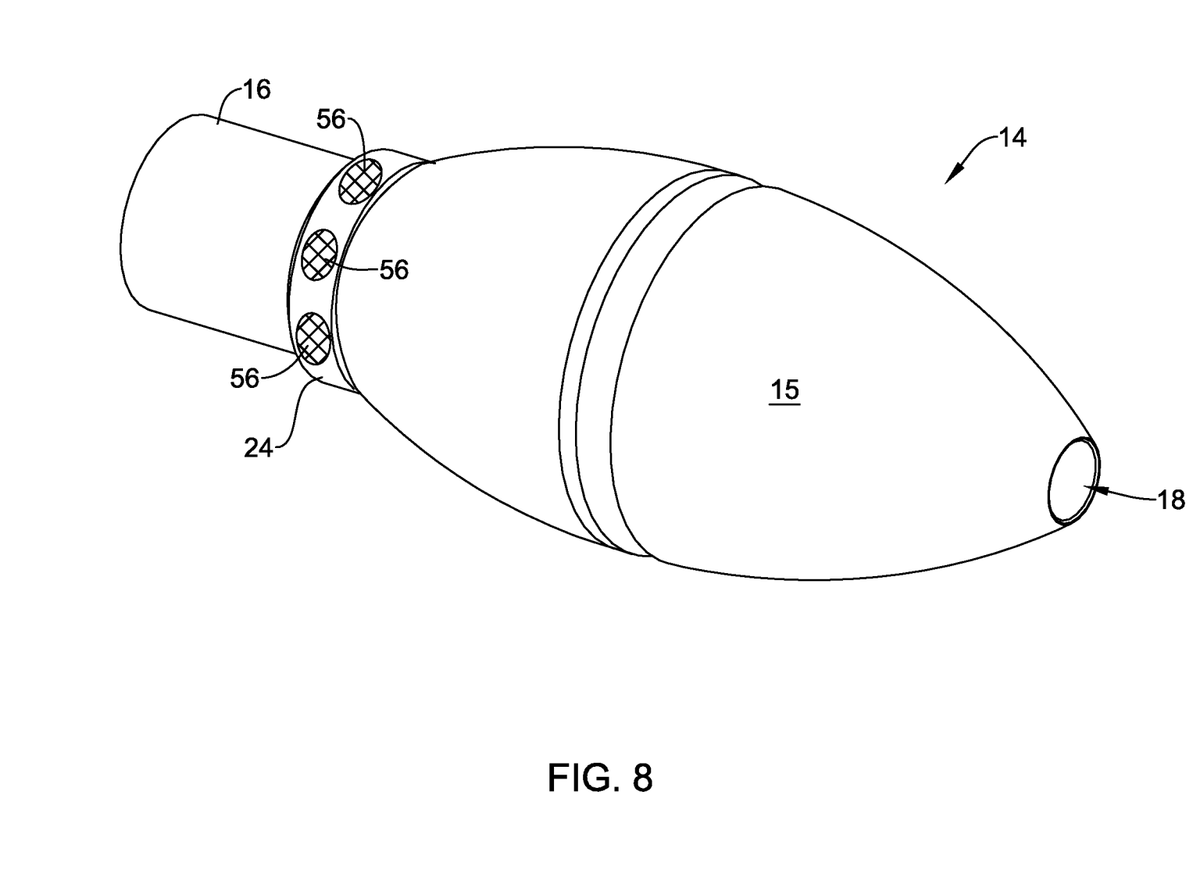
FIG. 8 is a perspective view of a portion of the example atherectomy device of FIG. 1, showing a welding pattern securing the cutting member to the coupler tube.
Figure 9:
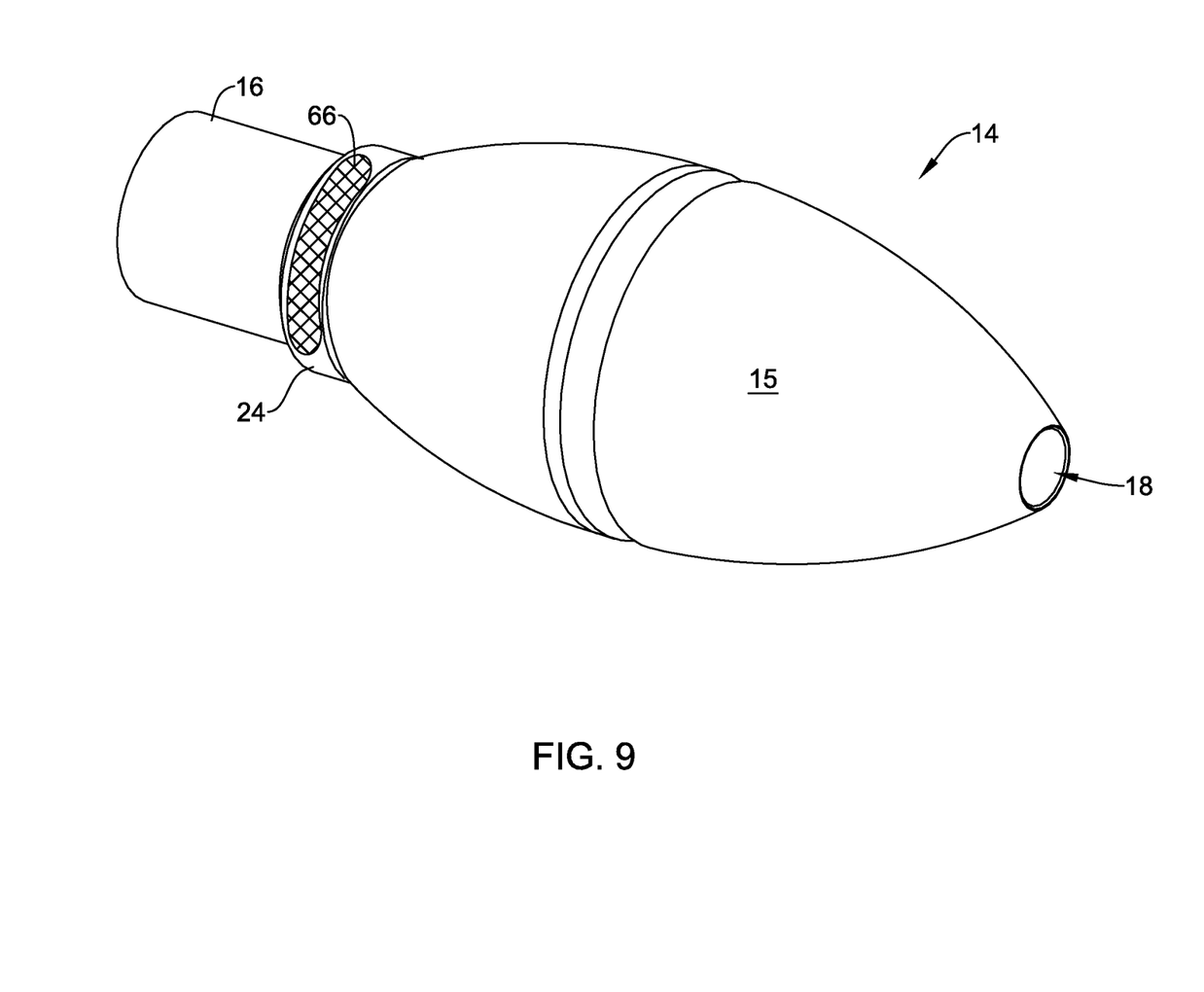
FIG. 9 is a perspective view of a portion of the example atherectomy device of FIG. 1, showing another welding pattern securing the cutting member to the coupler tube.

After the strain relief 16 has been welded to the elongate shaft 12, the cutting member 14 may be welded to the strain relief 16. While the strain relief member 16 is shown as extending proximally from under the cutting member 14 a distance, in some cases the strain relief member 16 may be flush with the cutting member 14, or may extend a distance of about a tenth of an inch or so. In some cases, the cutting member 14 may be secured to the strain relief member 16 by welding through the annular mounting portion 24. FIG. 8 and FIG. 9 provide illustrative but non-limiting examples of welding patterns that may be used in securing the cutting member 14 to the strain relief member 16. In FIG. 8, a series of spot welds 56 are shown. In some cases, the series of spot welds 56 extend all the way around the circumference of the annular mounting portion 24. In FIG. 9, a pair of circumferentially extending welds 66 are shown. In some cases, there may be a single circumferentially extending weld 66 that extends all the way around the circumference of the annular mounting portion 24. In some cases, there may be three or more circumferentially extending welds 66. These are just examples.

In some cases, the elongate shaft 12, the cutting member 14 and the strain relief member 16 may be formed of a variety of different metallic materials. In some cases, the elongate shaft 12, the cutting member 14 and the strain relief member 16 may be formed of materials that are suitable for welding together. For example, the strain relief member 16 may be formed of a material that is suitable for welding to the material from which the elongate shaft 12 is made. The cutting member 14 may be formed of a material that is suitable for welding to the material from which the strain relief member 16 is made. For example, this may mean welding a martensitic material to another martensitic material, or perhaps welding an austenitic material to another austenitic material. Nitinol is a unique material that has properties of both martensitic and austenitic materials, and can be laser welded to Nitinol. In some cases, the elongate shaft 12, the cutting member 14 and the strain relief member 16 may all be made of one or more particular types of stainless steels. As a particular but non-limiting example, the elongate shaft 12 may be formed of 304V stainless steel, the strain relief member 16 may be formed of 316L stainless steel and the cutting member 14 may be formed of 17-4PH stainless steel, all of which are austenitic materials.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

FIG. 10 illustrates an illustrative but non-limiting example of an interventional catheter assembly 410 with which the atherectomy devices described herein may, for example, be used. The interventional catheter assembly 410 includes a console unit 412, a controller 460, and a catheter system 432 having an operating head 440 located at or in proximity to the distal end of the catheter system. The controller 460 may be used to manipulate (e.g. advance and/or rotate) the catheter system 432 and operating head 440, or alternative controls may be provided. In some cases, at least some of the functionality of the console unit 412 may instead be built into a handle or other portion of the atherectomy device.

The console unit 412 incorporates an infusion pump 414 and an aspiration pump 416. During operation of the interventional catheter, an infusate conduit 418 draws fluid from an infusate reservoir 420 and operably contacts the infusion pump 414 to provide fluid through an infusion lumen in catheter system 432 to one or more infusion ports provided in proximity to the operating head. Similarly but in reverse, fluids with entrained particulates, if any, are withdrawn from the site of intervention through an aspiration lumen in the catheter system 432 and conveyed to an aspiration conduit 422, which is in operable contact with the aspiration pump 416, and communicates with the aspirate collection vessel 424. The console unit 412 may also provide a power source for operating the operating head and system components, or it may be in communication with an external power source. In some cases, the console unit 412 may provide power to the interventional catheter assembly and the controller 460 via a device power port 425 and power cord 426.

Various microprocessor, electronic components, software and firmware components may be provided within or in communication with the console unit for controlling operation of the interventional catheter as described herein. Software may be provided in a machine-readable medium storing executable code and/or other data to provide one or a combination of mechanisms to process user-specific data. Alternatively, various systems and components may be controlled using hardware or firmware implementations. Data storage and processing systems may also be provided in console unit 412. The console unit 412 is generally provided as a reusable assembly and is generally operated outside the sterile field. It may be mountable on a portable stand to facilitate convenient placement during interventions.

One function of the console unit 412 is to provide feedback of system and/or environmental conditions or operating parameters. The console unit may output operational information concerning operating conditions and feedback from the material removal site to the operator. In some cases, the console unit 412 may provide continuously updated output to an operator of operating parameters such as operating head rotation rate, which may include the actual run speed as well as the desired speed; operating head advance rate; aspiration rate and/or volume; infusion rate and/or volume; length of the body or matter to be removed that is traversed; and the like.

Certain automated and selectable control features may be implemented in the console unit 412. Preset routines or programs involving various operating parameters may be preselected, stored and selectable by an operator, for example. Thus, in some cases, the disclosed material removal system implements control features based on an operator's input of specified parameters. Specified parameters may include, for example: lesion length, lesion type and character, such as calcified, fibrotic, lipid/fatty and the like; historical factors, such as restenosis; rate of blood flow; volume of blood flow; percentage of restriction; lumen type and/or location; lumen diameter; desired rotation rate and/or rotation profile for the cutter assembly; desired advance rate and/or advance profile for the cutter assembly; desired aspiration rate and/or profile; desired infusion rate and/or profile; and the like. Based on the specified parameters input by the operator, the control unit may calculate and implement automated operating conditions, such as: cutter assembly rotation rate and profile; cutter assembly advance rate and profile; aspiration rate and profile; infusion rate and profile; cutter assembly size; and the like. Various system operating parameters, operating conditions, patient conditions, and the like may also be recorded and stored during interventions to preserve a record of the patient and intervention operational parameters.

In some cases, high efficiency aspiration may be provided in the interventional catheter systems disclosed herein. In certain cases, fluid and associated particulates are aspirated from the intervention site at rates of at least 15 ml/min of operating head run time and, in many cases, fluid and associated particulates are aspirated at rates of at least 25 ml/min of operating head run-time. In exemplary interventional catheter systems, the aspiration site may be more than a meter away from the controller 460 through an aspirate removal passageway located within the catheter system 432 and having a diameter of less than 0.10 inch, for example between about 0.050 to 0.070 inch. The distance that the aspirate travels between controller 460 and console unit 412 may be from about ½ meter to several meters, through an aspirate conduit that is between about 0.125 to about 1.0 inch in diameter. The blood and debris being aspirated are relatively viscous fluids, and achieving a relatively constant and high level of aspiration under these conditions is essential.

In one case, aspiration pump 416 may be a multi-lobed roller pump. The rotation rates of multiple rollers, or of a multi-lobed rotating structure, may be variable or selectable to control the aspiration rate and volume. Roller pumps permit fluid to flow in a conduit through the rollers of the pump at atmospheric pressure, and thus reduce or prevent the formation of bubbles and foam in the liquid being evacuated. Because the aspirate is at atmospheric pressure when it exits the roller pump, a simplified, atmospheric pressure collection vessel may be used rather than an evacuated collection vessel. A simple bag or another collection vessel, such as those used for collection of blood, may be used. For example, a collection bag 424 and a sealed aspiration conduit may be provided as part of a sterile disposable interventional catheter kit. A distal end of the aspiration conduit may be pre-mounted on and sealed to the controller 460. A proximal portion of the aspiration conduit is mounted on the aspiration pump prior to operation of the interventional catheter and the aspirate collection bag is mounted to or in proximity to the control module.

The infusion pump 414 may also be a multi-lobed roller pump employing variable or selectable rotation rates to control the infusion rate and volume. In some cases, a pressure cuff may be provided over a saline bag on an IV pole. A simple bag or another infusate reservoir, such as those used for intravenous infusions, may be used to supply the infusate. For example, an infusate reservoir 420 having a sealed conduit that is mounted in the infusion pump 416 during operation of the interventional catheter may be provided. In some cases, the sealed infusate conduit may be provided as part of the sterile disposable interventional catheter system and a distal end of the infusate conduit may be pre-mounted on and sealed to the controller 460. A proximal portion of the infusate conduit may be connected to an infusate reservoir, such as a saline bag, and mounted in proximity to the infusion pump prior to operation. A bubble detector 415 or a bubble trap (not illustrated) may be provided in association with the console unit 412 and the infusate conduit 418 to detect the presence of gas bubbles in the infusate. A control feature that automatically disables the infusion pump and/or power to the operating head may be activated upon detection of a fault (e.g. a bubble) in the infusate conduit.

The console unit 412 may also have control switches for activating and shutting down the aspiration pump and system, and for activating and shutting down the infusion pump and system. These control features may be provided as simple on/off switches. Alternatively, systems providing different levels or rates of aspiration and/or infusion that are selectable by an operator may be provided. In addition, the console unit 412 may be provided with a timing mechanism that determines, and displays, the elapsed time of operation of the operating head and/or the aspiration and infusion systems. The volumes of aspirate withdrawn and the volume of infusate introduced may also be detected and displayed by the console unit 412. Detection systems for monitoring the levels of aspirate and infusate in the respective reservoirs may be incorporated and alarms indicating an overfill condition for the aspirate collection system or a low supply condition for the infusate reservoir may be provided. Backup aspirate collection and infusate supply systems may also be provided.

In some cases, the console unit 412, together with the aspiration pump 416, the infusion pump 414 and the associated control and display features, may be provided as a separate, re-usable unit, that may be used as standard equipment in operating rooms, for example. In the system illustrated, the console unit 412 is not contaminated by contact with blood or aspirate during operation, and the power and control systems are durable and long-lasting and may be reused for many interventions. The console unit 412 may be provided in a housing designed to sit on a platform during operation, or the housing may be designed for mounting on a portable structure, such as an i.v. pole or another structure. The interventional catheter system, including the catheter system 432 with the operating head 440, the controller 460, the aspirate conduit 422, the aspirate collection vessel 424, and the infusate conduit 418 may be provided as a sterile, single use system kit.

The controller 460, which may be constructed from a durable, sterilizable material, such as hard plastic, may be provided in any convenient ergonomic design and constructed for placement in proximity to and/or in contact with the external body. In one instance, the controller may include an integrated handle for operator convenience in holding and supporting the controller during operation. The catheter system 432, exiting the controller 460, may be axially translatable with respect to the controller 460 as the operating head and catheter system are guided to a target material removal site. It will be appreciated that some of the control and operational features described herein with reference to the controller 460 may be provided in the console unit 412 and, likewise, some of the control and operational features described with reference to the console unit 412 may be provided in the controller 460.

FIG. 11 shows an example rotational atherectomy system 510 with which the atherectomy devices described herein may be used. The rotational atherectomy system 510 may include a rotational atherectomy device 512 and a controller 514 for controlling the rotational atherectomy device 512. The rotational atherectomy device 512 may include a housing 516 and an elongate shaft 518 extending distally from the housing 516 to a cutting member 520 located at a distal end of the elongate shaft 518. The elongate shaft 518 may include a drive shaft 524 to provide rotational motion to the cutting member 520. In some instances, the elongate shaft 518 may include an outer tubular member 522 having a lumen extending therethrough and the drive shaft 524 may extend through the lumen of the outer tubular member 522. The drive shaft 524, which may be fixed to the cutting member 520, may be rotatable relative to the outer tubular member 522 to rotate the cutting member 520. In some instances the axial position of the cutting member 520 relative to the outer tubular member 522 may be adjusted by moving the drive shaft 524 longitudinally relative to the outer tubular member 522. For example, the atherectomy device 512 may include an advancer assembly 526 positioned in the housing 516, or otherwise provided with the housing 516, that is longitudinally movable relative to the housing 516. The outer tubular member 522 may be coupled to the housing 516 while the drive shaft 524 may be coupled to the advancer assembly 526. Accordingly, the drive shaft 524 (and thus the cutting member 520) may be longitudinally movable relative to the outer tubular member 522 by actuating the advancer assembly 526 relative to the housing 516.

The rotational atherectomy device 512 may include a prime mover (not shown) to provide rotational motion to the drive shaft 524 to rotate the cutting member 520. For example, in some instances the prime mover may be a fluid turbine within the housing 516, such as provided with the advancer assembly 526. In other instances, however, the prime mover may be an electrical motor, or the like. The controller 514 may be used to control the prime mover. For example, the user may provide power to the prime mover and/or control the speed of rotation of the drive shaft 524 via the controller 514. For example, the front panel 528 of the controller 514 may include a user interface including a power switch, speed control mechanism (e.g., a speed control knob and/or buttons), a display, and/or other features for controlling the rotational atherectomy device 512. In some instances, the rotational atherectomy system 510 may include a remote control device 530, such as a foot pedal, a hand control, or other mechanism which may be used to control the power and/or speed to the prime mover, for example.

In instances in which the prime mover is a turbine, the rotational atherectomy system 510 may also include a pressurized fluid source 532 providing a pressurized fluid to the turbine to rotate the drive shaft 524. In some instances, as shown, the pressurized fluid source 532 may be a tank of pressurized fluid (e.g., compressed air), which may or may not include an air compressor. In other instances, the pressured fluid source 532 may be provided external of the rotational atherectomy system 510, such as from a wall outlet at the medical facility. The pressured fluid source 532 may be coupled to the controller 514 via a fluid conduit 534, which in turn is coupled to the rotational atherectomy device 512 via a fluid conduit 536. The controller 514 may regulate the flow and/or pressure of fluid through the fluid conduit 536 to the rotational atherectomy device 512 to control the speed of rotation of the drive shaft 524 and cutting member 520, for instance.

In instances in which the prime mover is an electric motor, the electric motor may be coupled to the controller 514 via an electrical connection to control the electric motor and/or provide electricity to the electric motor.

In some instances, the rotational atherectomy device 512 may include a speed sensor, such as an optical speed sensor, coupled to the controller 514 via a connector 538, such as a fiber optic connector to provide speed data to the controller 514. In other instances, an electronic sensor, such as a Hall Effect sensor, or other type of sensor may be used to sense the speed of the drive shaft 524 and cutting member 520. The speed data may be displayed, such as on the front panel 528 and/or the controller 514, and/or used to control the speed of the cutting member 520, such as maintaining a desired speed of the cutting member 520 during a medical procedure.

In some instances, the rotational atherectomy system 510 may be configured to infuse fluid through the elongate shaft 518 to the treatment site and/or aspirate fluid through the elongate shaft 518 from the treatment site. For example, the rotational atherectomy system 510 may include a fluid supply 540 for providing a flow of fluid through a lumen of the elongate shaft 518 to a treatment site. In some instances the fluid supply 540 may include a saline bag 542 which may be pressurized by a pressure cuff 544 to provide a pressurized fluid (e.g., saline) to the rotational atherectomy device 512 through a fluid supply line 546. In other instances, an infusion pump, such as a peristaltic pump, may be used to deliver pressurized fluid to the rotational atherectomy device 512. Additionally or alternatively, in some cases the rotational atherectomy system 510 may be configured to aspirate fluid from the treatment site. For example, the rotational atherectomy system 510 may include an aspiration pump, such as a peristaltic pump, to generate a vacuum to aspirate fluid through a lumen of the elongate shaft 518 to a fluid collection container (not shown), if desired.

In some instances, the elongate shaft 518 of the rotational atherectomy device 512 may be advanced over a guidewire 548 to a treatment site. For example, the drive shaft 524 may include a guidewire lumen through which the guidewire 548 may pass.

Additionally or alternatively, the elongate shaft 518 may be advanced through a lumen of a guide catheter to a treatment site.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The scope of the disclosure is, of course, defined in the language in which the appended claims are expressed.

What is claimed is:

1. An atherectomy device, comprising:
   an elongate shaft having a proximal end region and a distal end region, the elongate shaft including a longitudinal axis, the elongate shaft comprising a drive coil having a plurality of coil windings extending in a first helical direction;
   a strain relief member secured to the distal end region of the elongate shaft, the strain relief member comprising a tubular member welded to the drive coil via one or more welds that extend helically at least partially around the tubular member in order to engage multiple coil windings; and
   a cutting member secured to the strain relief member and defining an outer surface.

2. The atherectomy device of claim 1, wherein the one or more welds securing the tubular member to the drive coil are angled in the first helical direction, but at a different pitch.

3. The atherectomy device of claim 1, wherein the one or more welds securing the tubular member to the drive coil are angled in a second helical direction different from the first helical direction.

4. The atherectomy device of claim 1, wherein the elongate shaft comprises a stainless steel.

5. The atherectomy device of claim 1, wherein the strain relief member comprises a stainless steel.

6. The atherectomy device of claim 1, wherein the strain relief member comprises a stainless steel.

7. The atherectomy device of claim 1, further comprising an abrasive material disposed on at least a portion of the outer surface of the cutting member.

8. An atherectomy device, comprising:
   an elongate drive coil having a proximal end region and a distal end region, the elongate drive coil having a coil winding extending in a first helical direction, the elongate drive coil having a coil pitch;
   a tubular member welded to the distal end region of the elongate drive coil via one or more helical welds that extend helically at least part way around the tubular member; and
   a cutting member welded to the tubular member.

9. The atherectomy device of claim 8, wherein the cutting member comprises a curved cutting surface and an annular mounting surface, and the cutting member is welded to the tubular member via one or more welds extending through the annular mounting surface.

10. The atherectomy device of claim 9, wherein the one or more welds extending through the annular mounting surface comprise a circumferential weld extending about the annular mounting surface.

11. The atherectomy device of claim 9, wherein the one or more welds extending through the annular mounting surface comprise a plurality of distinct welds.

12. The atherectomy device of claim 8, wherein the one or more helical welds each intersect a plurality of adjacent coil windings.

13. The atherectomy device of claim 8, wherein the one or more helical welds each extend in the first helical direction, but at a different pitch than the coil pitch.

14. The atherectomy device of claim 8, further comprising an abrasive material disposed on at least a portion of the cutting member.

15. An atherectomy device, comprising:
   an elongate drive coil having a proximal end region and a distal end region, the elongate drive coil having a longitudinal axis and a coil pitch relative to the longitudinal axis;

a tubular member welded to the distal end region of the elongate drive coil via one or more helical welds that extend helically at least part way around the tubular member, the one or more helical welds extending at a weld pitch relative to the longitudinal axis; and a cutting member welded to the tubular member.

16. The atherectomy device of claim 15, wherein the weld pitch is different from the coil pitch such that at least one of the one or more helical welds engage a plurality of adjacent coil windings.

17. The atherectomy device of claim 15, wherein the cutting member includes an abrasive cutting surface.

\* \* \* \* \*